(12) United States Patent
Kramer et al.

(10) Patent No.: US 12,403,281 B2
(45) Date of Patent: Sep. 2, 2025

(54) BONE-CONDUCTIVE SOUND THERAPY DEVICE AND METHOD

(71) Applicant: Simple Learning, LLC, Columbus, IN (US)

(72) Inventors: Tina S. Kramer, Columbus, IN (US); Kenneth L. Kramer, Columbus, IN (US); Thomas Walker, Shenzhen (CN)

(73) Assignee: SIMPLE LEARNING, LLC, Columbus, IN (US)

( * ) Notice: Subject to any disclaimer, the term of this patent is extended or adjusted under 35 U.S.C. 154(b) by 1054 days.

(21) Appl. No.: 17/355,646

(22) Filed: Jun. 23, 2021

(65) Prior Publication Data

US 2021/0393916 A1 Dec. 23, 2021

Related U.S. Application Data

(60) Provisional application No. 63/042,805, filed on Jun. 23, 2020.

(51) Int. Cl.
| | | |
|---|---|---|
| *A61M 21/00* | (2006.01) | |
| *A61M 21/02* | (2006.01) | |
| *H04R 1/02* | (2006.01) | |
| *H04R 3/00* | (2006.01) | |
| *H04R 9/06* | (2006.01) | |

(52) U.S. Cl.
CPC ............. *A61M 21/00* (2013.01); *H04R 1/025* (2013.01); *H04R 1/026* (2013.01); *H04R 3/00* (2013.01); *A61M 2021/0027* (2013.01); *A61M 21/02* (2013.01); *A61M 2209/088* (2013.01); *H04R 9/06* (2013.01); *H04R 2460/13* (2013.01)

(58) Field of Classification Search
CPC .................................. A61M 2021/0022–0038
See application file for complete search history.

(56) References Cited

U.S. PATENT DOCUMENTS

| | | |
|---|---|---|
| 9,589,478 B2 | 3/2017 | Davis |
| 2020/0245931 A1* | 8/2020 | Chmelik .............. A61B 5/6831 |
| 2021/0178112 A1* | 6/2021 | Ning ...................... G16H 20/30 |

FOREIGN PATENT DOCUMENTS

WO WO-2021243564 A1 * 12/2021

OTHER PUBLICATIONS https://healthhackers.org/handson/trialling-the-sensate-pebble (Year: 2019).*
https://www.youtube.com/watch?v=tEnCf5CYWgs (Year: 2019).*
https://www.youtube.com/watch?v=X4pJhYIQXFw (Year: 2020).*

\* cited by examiner

*Primary Examiner* — Thaddeus B Cox
(74) *Attorney, Agent, or Firm* — Brannon Sowers & Cracraft PC

(57) ABSTRACT

A wearable sound therapy device includes a housing, and a loop cord coupled to the housing for supporting the sound therapy device pendant from the neck of a user upon a torso of the user. Audio electronics are resident in the housing and include a bone-conduction transducer, an audio file storage medium storing an audio file, a power supply, and a transducer control unit structured to energize the bone-conduction transducer based on the stored audio file to bone-conduct sounds to the body of the user. The stored audio file can include a compressed audio file such as an MP3 or MP4 file of pure tone sounds.

13 Claims, 8 Drawing Sheets

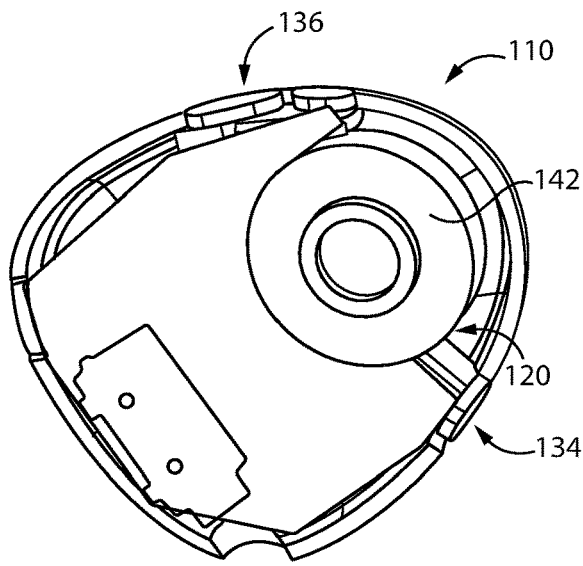
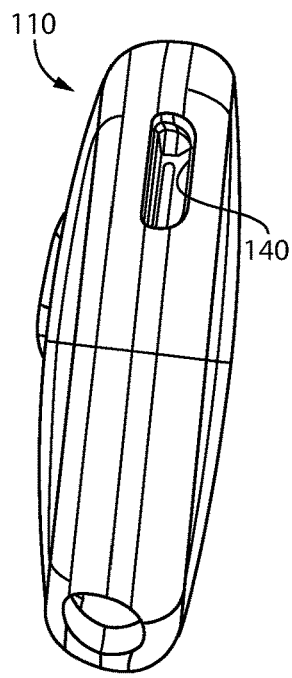
FIG. 16
FIG. 17
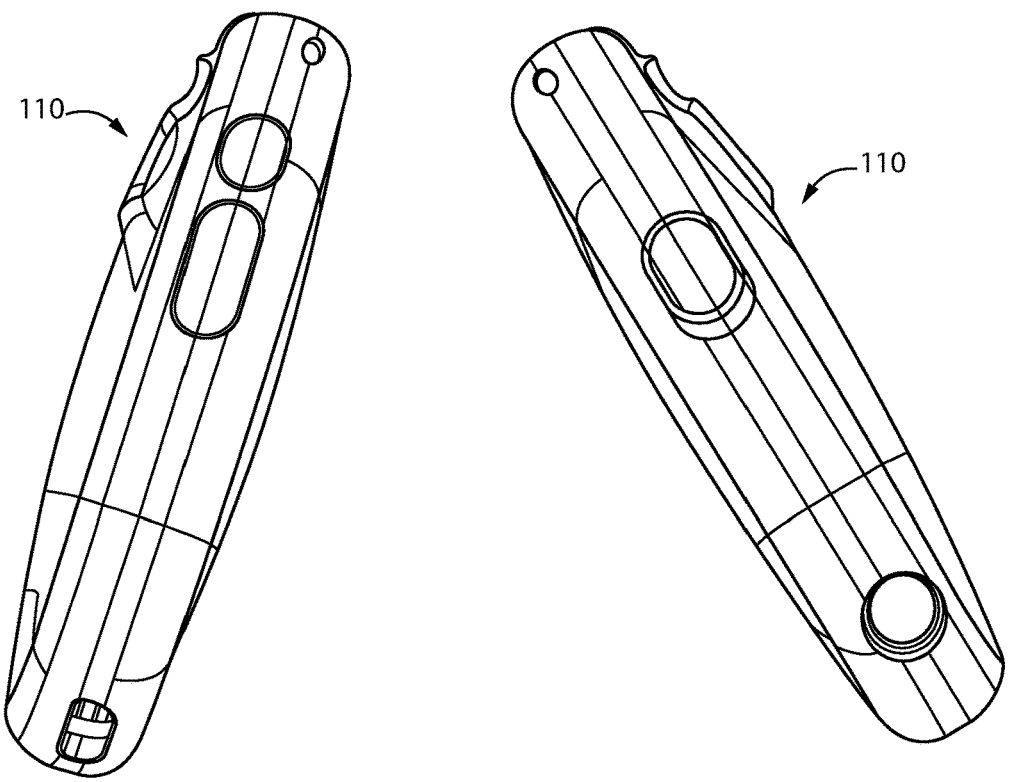
FIG. 18
FIG. 19

BONE-CONDUCTIVE SOUND THERAPY DEVICE AND METHOD

CROSS-REFERENCE

This application claims the benefit of U.S. Provisional Patent Application No. 63/042,805 titled "BONE-CONDUCTIVE SOUND THERAPY DEVICE AND METHOD," filed Jun. 23, 2020, the entire disclosure of which is expressly incorporated by reference herein.

TECHNICAL FIELD

The present disclosure relates generally to a wearable sound therapy device, and more particularly to a wearable sound therapy device including audio electronics having a bone-conduction transducer structured to play stored audio files.

BACKGROUND

Therapeutic use of sound in the treatment of various conditions, or merely for enjoyment, ranges from the use of music to exposure to predefined patterns of non-musical tones for the treatment of various medical and psychological conditions. A variety of white noise-producing devices and devices with a menu of prerecorded sounds of nature or the like are well known and widely commercially available for purposes of stress reduction, improved sleep, enhanced mental clarity, and the like. In formal clinical applications instruments such as gongs, bowls, tuning forks, and other sound producing devices are used to apply sound for various purported therapeutic and healing purposes.

Various known sound therapy devices propose to address states or conditions of a user through the application of audible air-conducted sound and/or body-conducted sound. U.S. Pat. No. 9,589,478 to Davis proposes a Natural Orientation Induction Tool Apparatus and Method. In the Davis concept an apparatus for training learning disabled subjects induces sound waves into a body of a user through the user's ears as well as through a liquid or solid in contact with tissues of the user's body. Apparently, a gel pad is attached to the user's back for the conduction of sound through the user's body tissues.

Other devices relating to sound therapy are directed more to a user's sense of hearing itself. United States Patent Application Publication No. 2014/0193011A1 to Parker is directed to a bone conduction device having an external component including a sound processor and transducer configured to generate mechanical forces apparently to conduct sound to a recipient's bone to generate a hearing percept via bone conduction.

SUMMARY OF THE INVENTION

In one aspect, a wearable sound therapy device includes a housing, and a loop cord coupled to the housing for supporting the sound therapy device pendant from the neck of a user upon a torso of the user. The sound therapy device further includes audio electronics resident in the housing and including a bone-conduction transducer, an audio file storage medium storing an audio file, and a power supply. The audio electronics further include a transducer control unit structured to energize the bone-conduction transducer based on the stored audio file.

In another aspect, a method for sound therapy includes reading a stored audio file from an audio file storage medium of a sound therapy device having a cord positioned about the neck of a user, and energizing a transducer in the sound therapy device to vibrate based on the audio file. The method further includes bone-conducting sound to the user based on the energizing of the transducer.

In still another aspect, a wearable sound therapy device includes a housing having a cord connector for attaching a loop cord to support the sound therapy device about a user's neck, such that the sound therapy device is freely positionable in contact with the body of the user at a range of locations. The audio electronics include a transducer, an audio file storage medium storing an audio file, and a power supply. The audio electronics further include a transducer control unit structured to energize the transducer to vibrate based on the stored audio file in a manner that bone-conducts sound to the body of the user.

BRIEF DESCRIPTION OF THE DRAWINGS

FIG. 16 is an open view of portions of the sound therapy device of FIGS. 14 and 15;

FIG. 17 is a first side view of the sound therapy device of FIGS. 14 and 15;

FIG. 18 is another side view of the sound therapy device of FIGS. 14 and 15;

FIG. 19 is yet another side view of the sound therapy device of FIGS. 14 and 15.

DETAILED DESCRIPTION

Figure 1:
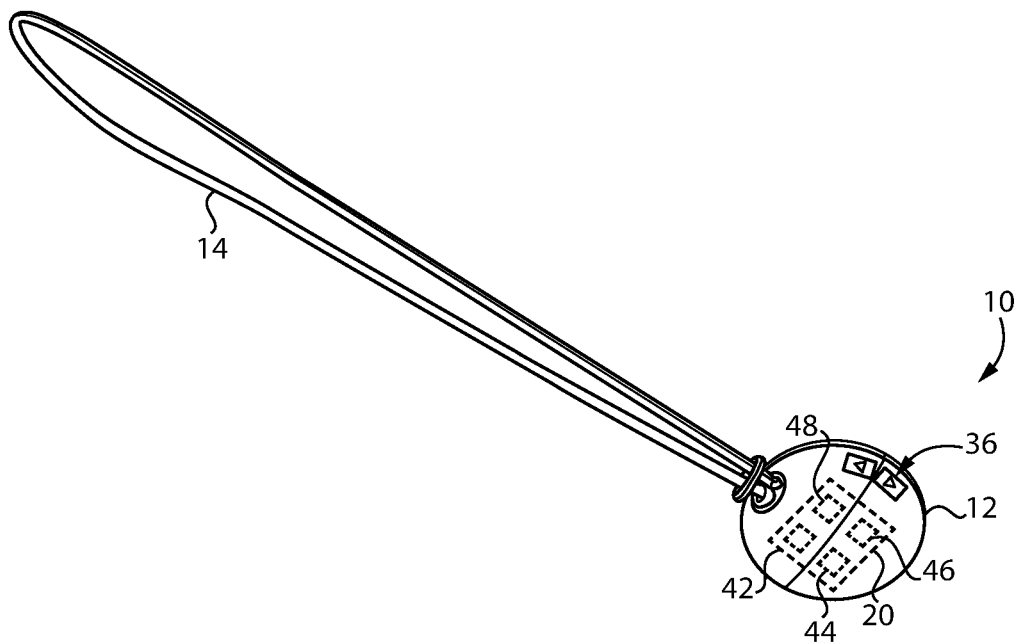
FIG. 1 is a perspective view of a sound therapy device, according to one embodiment.
Figure 2:
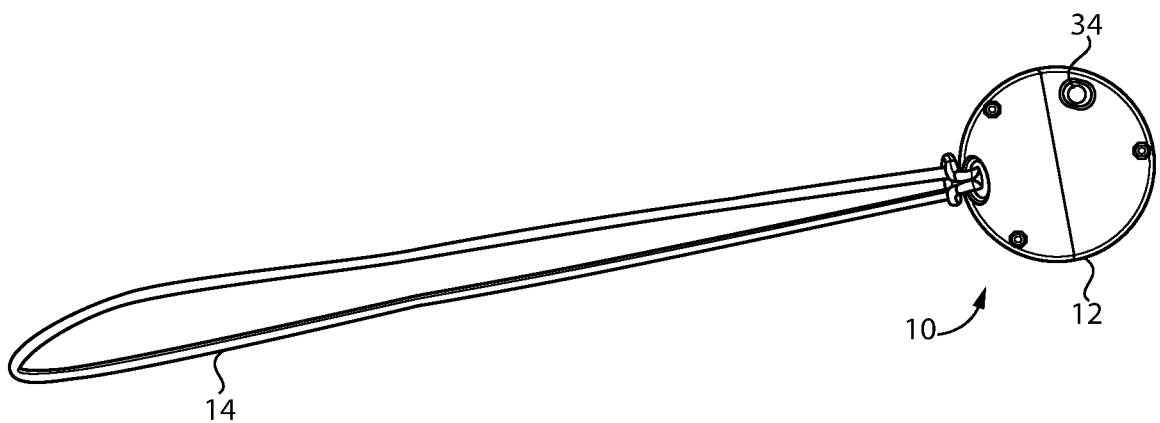
FIG. 2 is another perspective view of a sound therapy device, according to one embodiment.

Referring to FIGS. 1 and 2, there is shown a wearable sound therapy device 10, according to one embodiment.

Wearable sound therapy device 10 (hereinafter "device 10") includes a housing 12, and a loop cord 14 coupled to and attached to housing 12, for supporting device 10 pendant from the neck of user upon a torso of the user. It is contemplated that device 10 will be worn in the manner of a necklace with loop cord 14 formed of a suitable fabric, polymeric, leather or other material and having a length sufficient to position housing 12 in contact with a user's breast bone when worn. A user or caregiver can manipulate device 10 to position housing 12 at a range of locations in contact with other parts of the user's body, including his/her head, however, as noted contact with the user's torso including the user's breast bone, collar bones, neck, rib cage, or other bones is considered a practical application. Loop cord 14 may be equipped with various mechanisms including cinches or the like for adjusting its length.

Device 10 further includes audio electronics 20 resident in housing 12, and in a practical implementation including a bone-conduction transducer 42, an audio file storage medium 44 storing an audio file, a power supply 46, and a transducer control unit 48 structured to energize bone-conduction transducer 42 based on the stored audio file as further discussed herein. Also shown in FIGS. 1 and 2 are an on/off button or switch 34, and volume control buttons 36 including one button which can be pressed to increase volume and another button which can be pressed to decrease volume. A slider, a thumbwheel, or any of a variety of other structures could be used for volume control or for turning device 10 on or off.

Figures 3, 4:
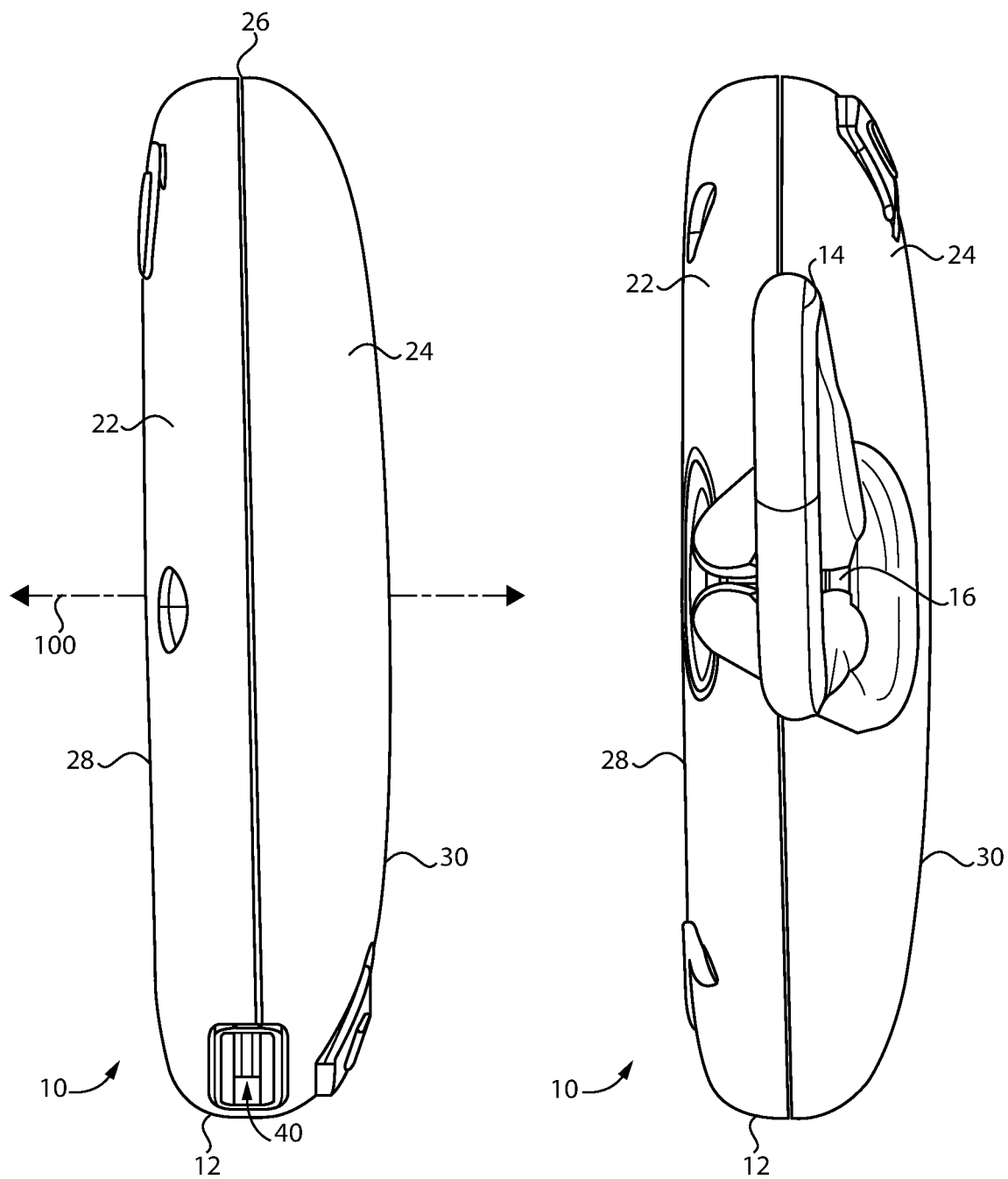
FIG. 3 is a forward end view of a sound therapy device, according to one embodiment.
FIG. 4 is a rearward end view of a sound therapy device, according to one embodiment.

Referring also now to FIGS. 3 and 4 device 10 includes housing 12 as noted above. Housing 12 can include a first housing half 22 and a second housing half 24. The use of the term "half" should not be understood to mean that either portion of housing 12 necessarily makes up one half of housing 12, but merely to illustrate that there are two generally equivalent portions of housing 12 in the illustrated embodiment. First housing half 22 and second housing half 24 may abut one another at a split line 26, and together form an interior cavity wherein audio electronics 20 are positioned. First housing half 22 includes an outer surface 28, and second housing half 24 includes an outer surface 30. Housing 12 may be disc-shaped, such that an outer perimeter substantially defines a circle, however, the present disclosure is not thereby limited and a variety of other housing configurations are contemplated herein. Outer surface 28 may be substantially planar, with outer surface 30 being dome shaped. Each of outer surfaces 28 and 30 could be planar or each could be dome shaped in other embodiments. Housing 12 also includes a cord connector 16 as shown in FIG. 4, whereby loop cord 14 is attached to housing 12. In the illustrated embodiment cord connector 16 includes a hole formed in part by each of first housing half 22 and second housing half 24 through which loop cord 14 may be threaded. Loop cord 14 could be tied through the hole, clipped or buttoned to housing 12, or attached by any other suitable strategy.

Figure 5:
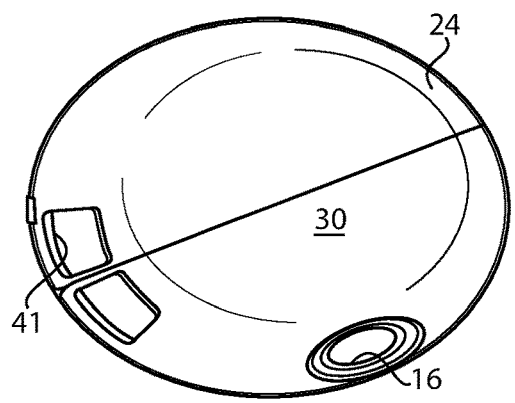
FIG. 5 is an elevational view of a housing half for a sound therapy device, according to one embodiment.
Figure 6:
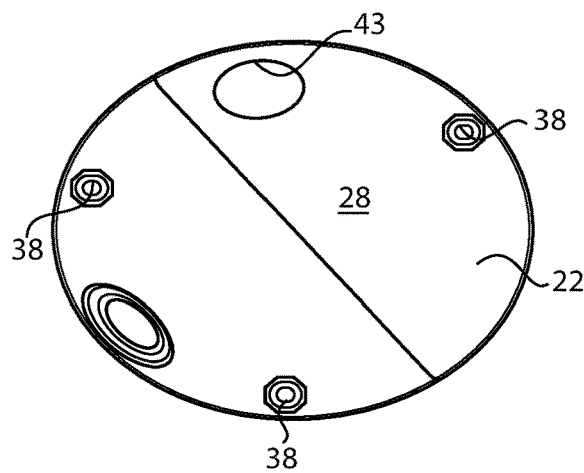
FIG. 6 is an elevational view of another housing half for a sound therapy device, according to one embodiment.
Figure 7:
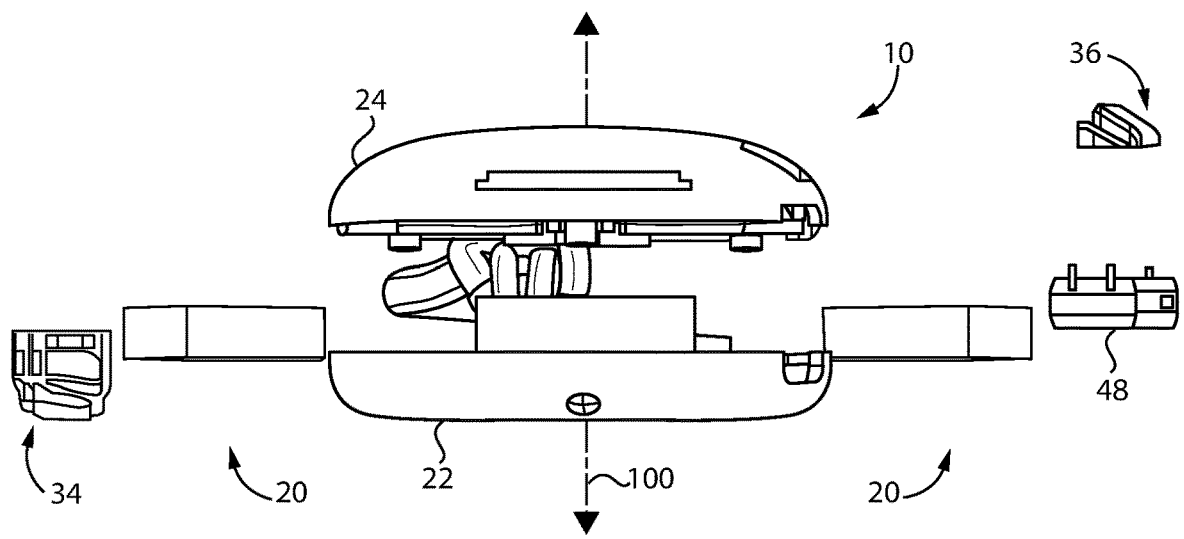
FIG. 7 is an exploded view of a sound therapy device, according to one embodiment.

Referring also now to FIGS. 5-13, there are shown additional features of device 10 and in further detail. Second housing half 24 is shown in FIG. 5, and includes button holes 41 formed therein for receipt of volume control buttons 36. Another button hole 43 is formed in first housing half 22 for receipt of on/off switch 34. Optionally, volume control buttons 36 and/or on/off switch 34 may be recessed within button holes 41, 43 so as to prevent accidental activation of the buttons. Fastener holes 38 extend through first housing half 22 and are structured to receive fasteners for attaching first housing half 22 and second housing half 24 together.

As can be seen from the exploded views and partial view of FIGS. 7-13, power supply 46 may include a plurality of battery cells 47. Battery cells 47 may be attached to and/or seated in battery seats 49 formed in first housing half 22. A printed circuit board (PCB) 56 is captured between first housing half 22 and second housing half 24. Additional electronics components of audio electronics 20 are associated with on/off switch 34 and volume control buttons 36. These components are not separately numbered and enable the electrical connections and mechanical connections with printed circuit board 56 necessary for their intended functions.

Figure 11:
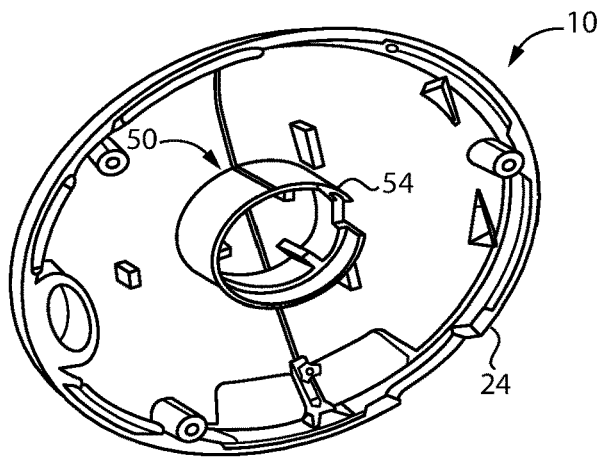
FIG. 11 is a partial view of a housing and transducer holder for a sound therapy device, according to one embodiment.
Figure 12:
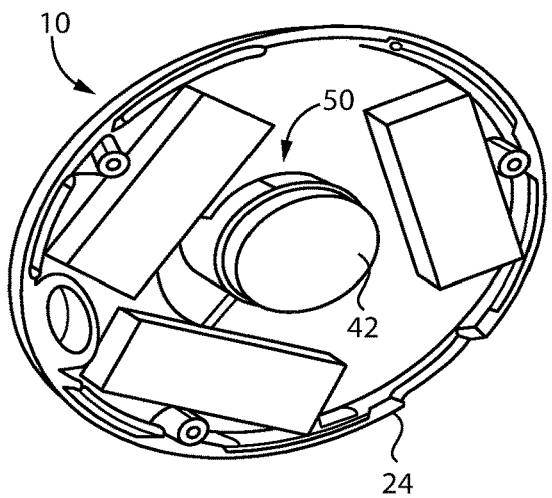
FIG. 12 is a view similar to FIG. 11 showing a transducer seated in the transducer holder in a sound therapy device, according to one embodiment.
Figure 13:
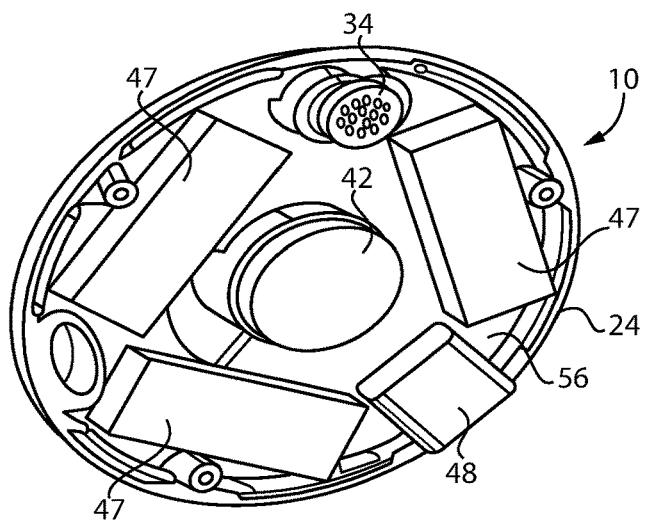
FIG. 13 is a view similar to FIG. 12 showing additional audio electronics components.
Figure 14:
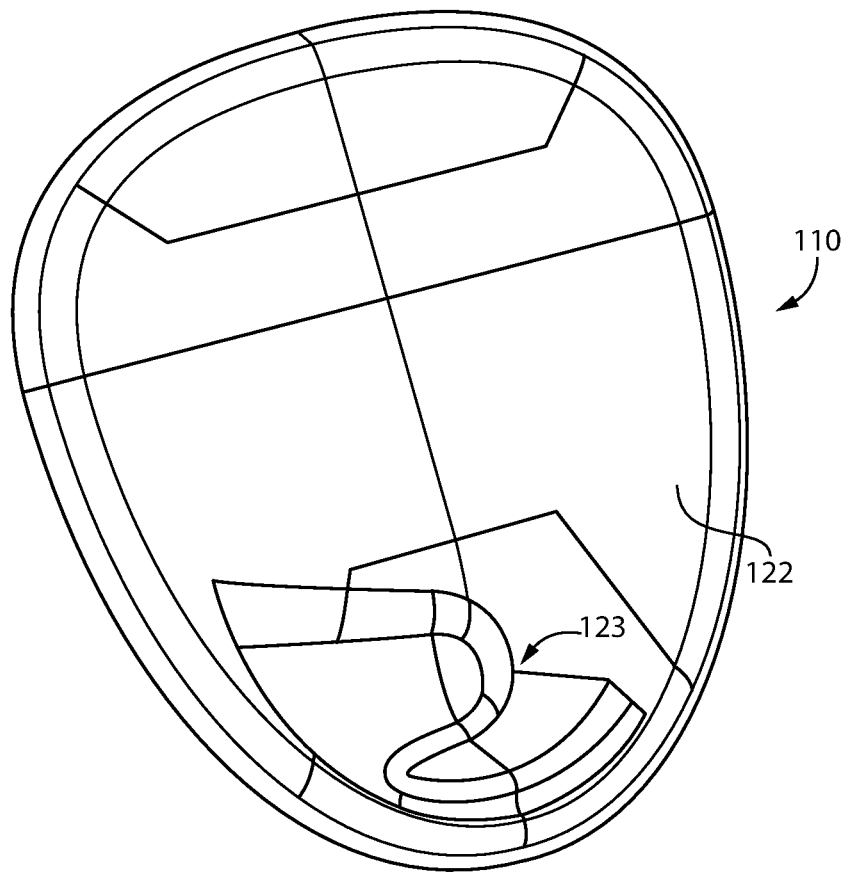
FIG. 14 is a top elevational view of a sound therapy device, according to one embodiment.
Figure 15:
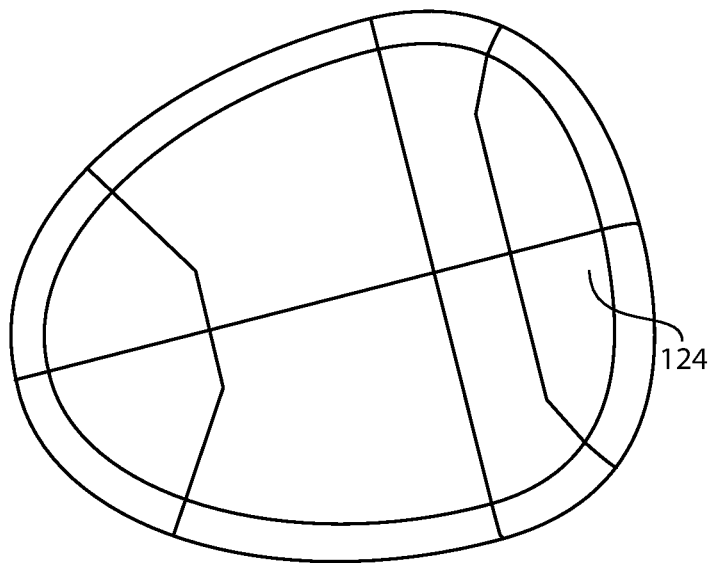
FIG. 15 is a bottom elevational view of a sound therapy device, according to one embodiment.
Figure 20:
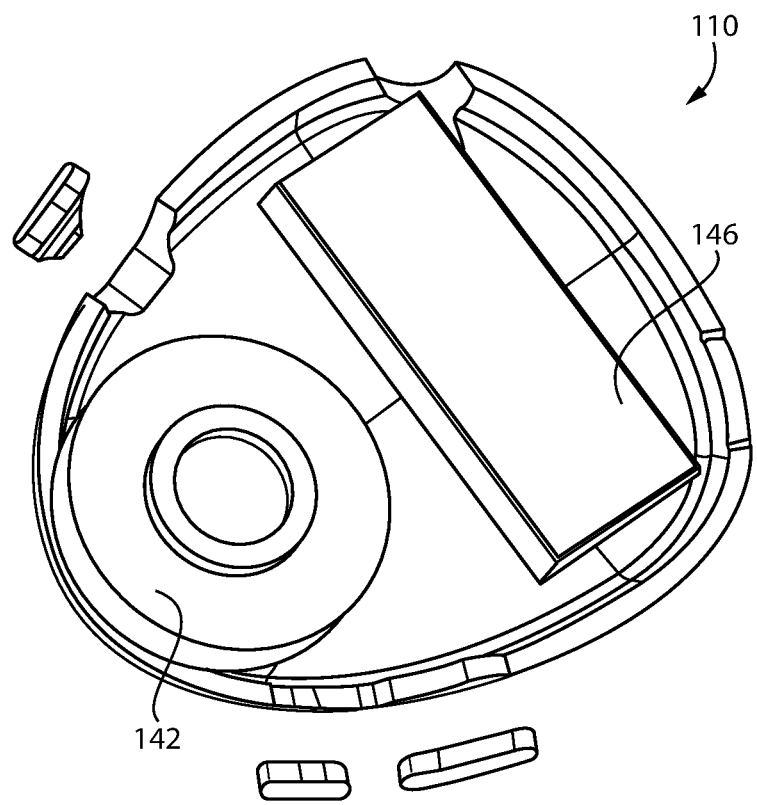
FIG. 20 is an exploded view of portions of the sound therapy device of FIG. 15.

As can be seen in FIG. 11, device 10 may include a centrally located transducer holder 50. Transducer 42 can be seated within transducer holder 50 and supported in housing 12 such that vibrations produced by energizing transducer 42 can be transmitted to the body of a user such as by contacting a contact surface 52, shown in FIG. 10, in the opposite housing half. Another way to understand this construction is that transducer 42 may be supported in one housing half and in contact with but not directly attached to another housing half, enabling vibrations produced by energizing transducer 42 to be conducted through housing 12 to the body of a user. A user or caregiver can position device 10 where desired in contact with the body of the user, and press device 10 against the user's body with a desired pressure to vary a volume or character of sound conducted to the user's body. Optionally, the housing 12 may include an indicia such as a color or symbol which indicates where the transducer 42 contacts the housing 12. Transducer holder 50 can include an arcuate wall 54 as shown in FIG. 11, and suitable positioning and retention elements for capturing transducer 42 therein. Battery cells 47 can be generally distributed circumferentially around transducer holder 50, enabling a compact package configuration. As also depicted in FIG. 13 transducer control unit 48 can be mounted upon printed circuit board 56 and positioned between two adjacent ones of battery cells 47.

Transducer control unit 48 can include any suitable central processing unit such as a microprocessor or a microcontroller. A connection port, such as a USB port type-C, a micro USB port, or still another, is shown at numeral 40 in FIG. 3, for example. Port 40 can be a charging port only in some embodiments enabling device 10 to be charged by connecting to a user's computer, a wall outlet, or the like. In other embodiments, port 40 could enable connecting to a user's computer for uploading audio or other files to device 10, downloading files, diagnostics such as frequency and/or duration of use of device 10, or for other purposes. In still other embodiments the device 10 may include hardware allowing for the transfer of files using wireless protocols.

Figure 8:
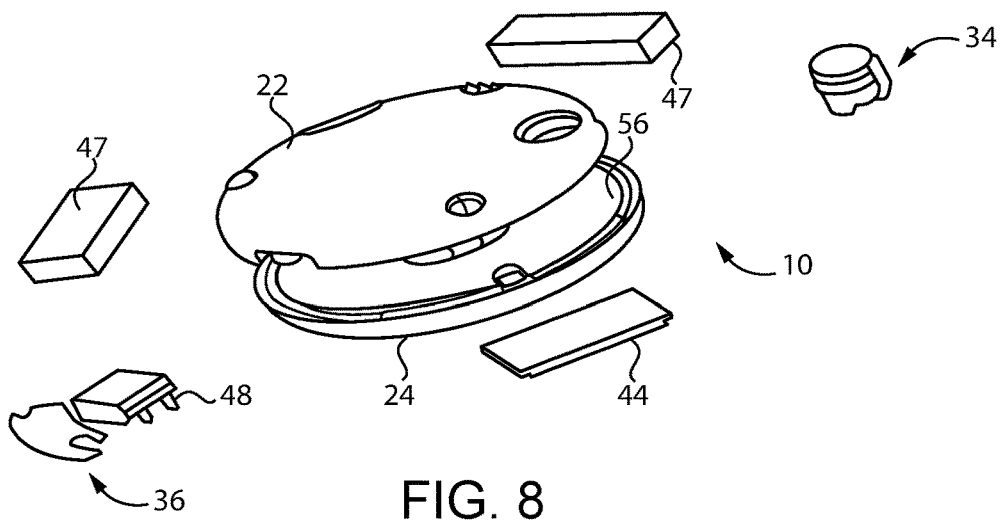
FIG. 8 is another exploded view of a sound therapy device, according to one embodiment.
Figure 9:
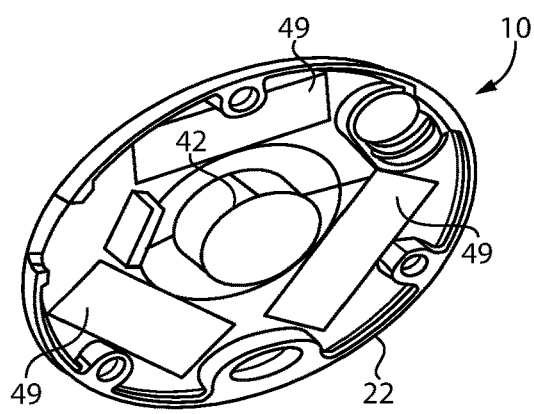
FIG. 9 is a partial view of a housing half and audio electronics in a sound therapy device, according to one embodiment.
Figure 10:
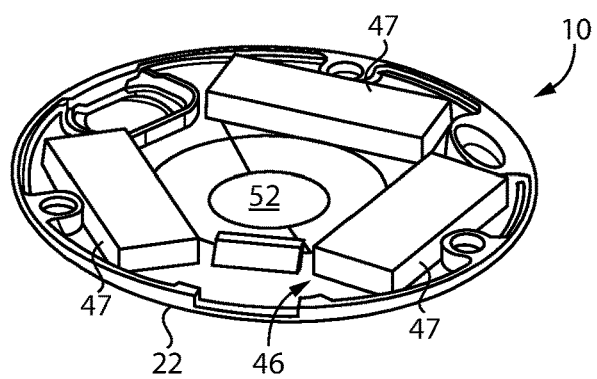
FIG. 10 is another partial view of a housing half and audio electronics for a sound therapy device, according to one embodiment.

An audio file storage medium is shown at numeral 44 in FIG. 8. Audio file storage medium 44 stores at least one audio file, as noted above, with transducer control unit structured to energize transducer 42 based on the stored audio file. In a practical implementation strategy, transducer control unit 48 reads the stored audio file from storage medium 44, and energizes an electromagnetic coil or other structure of transducer 42 to vibrate transducer 42 based on the stored audio file. Vibrating transducer 42 can in turn transmit vibrations to housing 12, and in turn transmit those vibrations to a user's bone structures for bone-conduction to the inner ear in a well-known manner. Storage medium 44 can include any suitable machine-readable storage medium such as RAM, ROM, flash, DRAM, SDRAM, EEPROM, or still another volatile or non-volatile memory.

In a further practical implementation the stored audio file includes a compressed audio file. The stored audio file may be an MP3 or MP4 file of tuning fork sounds, or still another compressed audio file such as an OGG Vorbis file or an AAC (Advanced Audio Coding) file. A lossless compression file such as FLAC (Free Lossless Audio Codec), ALAC (Apple Lossless Audio Codec) or even an uncompressed audio file could be used in some instances. A tuning fork sound according to the present disclosure could sound the note of C=528 Hz, although the present disclosure is not thereby limited. A range of sound frequencies that might be produced playing one or more stored audio files may be from 350 Hz to 900 Hz in some embodiments. The tuning fork sounds could range through a hole or partial note scale, up and then down, repeat the same tone, or any other combination of pitches, timbre, and volume.

Referring now to FIGS. 14-20, there is shown a sound therapy device 110 according to another embodiment. Sound therapy device 110 has a number of similarities with sound therapy device 10 discussed above, but differences as to housing shape and contour. A housing 122 of sound therapy device 110 includes an arcuate, generally S-shaped protrusion 123 upon one side, but is smooth upon an opposite side. An on/off switch is shown at numeral 134, and volume control buttons are shown at numeral 136. A bone-conduction transducer 142 is situated along with other audio electronics 120 within housing 122. A port 140 for charging or other purposes is also provided.

INDUSTRIAL APPLICABILITY

In use, device 10 may be suspended with cord 12 from the neck of a user such that device 10 is in contact with the torso of the user. When turned on, device 10 may operate by transducer control unit 48 reading, from audio file storage medium 44, a stored audio file, and energizing transducer 42 to vibrate based on the audio file. Those skilled in the art will appreciate that a bone-conducting transducer will typically include no speaker cone, but instead a voice coil wrapped around an electro-magnetically moveable pin or actuator that contacts another object to produce vibrations at a frequency based on energizing and deenergizing or other electrical manipulation of the transducer voice coil. Vibrating transducer 42 in turn vibrates housing 12 as discussed herein, and produces vibrations that can be conducted into the body of the user.

It has been discovered that bone conduction of sound can provide various therapeutic benefits without requiring production of sound that is perceptible, or only mildly perceptible, to third parties. Accordingly, one application of the present disclosure is considered to be the use and implementation of sound therapy for a user without communicating the therapeutic sound to others.

In one application of the disclosed technology the device 10 may be used to reproduce a pure tone similar to that produced by a tuning fork. Musical tones such that those produced by a plucked string or vibrating reed are composed of a number of harmonically related sinusoidal waves. In contrast, a pure tone includes only one such sinusoidal waveform. Tuning forks produce relatively pure tones which have few overtone modes which tend to die out quickly leaving only a pure tone at the fundamental frequency of the tuning fork. Many people find pure tones similar to those produced by tuning forks to have beneficial effects particularly when experienced through bone conduction. The exact frequency of a tone reproduced by a device according to the disclosed technology may vary from user to user depending on personal preference. Optionally, a device may include audio files for producing more than one tone if a user derives benefits from different tones or from certain tones in particular situations. For example, a user might find one tone lessens anxiety when in a crowd whereas a different tone lessens stress experienced when in an enclosed space such as an elevator.

Devices such as those described herein may be used in a variety of settings where the use of such devices may have beneficial therapeutic effects. For example, a user who suffers from panic attacks when in crowds may wear a loop cord around the user's neck such that the device rests against the breastbone. Optionally the device may be worn under clothing so as not to be visible to others. When the user begins to feel increased anxiety from being around people the user may activate the device and hold it against their beast bone to experience the tone produced by the device directly through bone conduction. Because it is experience through bone conduction the volume of the tone may be low enough so that people standing near the user may not be able to hear the tone. If the device is worn under the user's clothing an outside observer would simply see the user holding a hand against their chest which allows the user to experience the benefits of the device without drawing attention to themselves (which might otherwise increase their anxiety). In other situations a user might activate the device and hold it against their jaw, wrist, or other location on their body where a bone is near enough to the surface of the skin for bone conduction to be effective and/or where a particular user might gain therapeutic benefits.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. As noted above, the teachings set forth herein are applicable to a variety of different pillows, pillow covers, and pillow or pillow cover systems having a variety of different structures than those specifically described herein. Other aspects, features and advantages will be apparent upon an examination of the attached drawings and appended claims. As used herein, the articles "a" and "an" are intended to include one or more items, and may be used interchangeably with "at least one." Where only one item is intended, the term "one" or similar language is used. Also, as used herein, the terms "has," "have," "having," or the like are intended to be open-ended terms.

What is claimed is:

1. A wearable sound therapy device comprising:
   a housing having a first housing half and a second housing half attached to the first housing half and together forming a housing cavity;
   a loop cord coupled to the housing for supporting the sound therapy device from the neck of a user upon a torso of the user; and
   audio electronics resident in the housing, the audio electronics including:
      a bone-conduction transducer in contact with the housing;
      an audio file storage medium storing an audio file;
      a power supply; and
      a transducer control unit structured to energize the bone-conduction transducer based on the stored audio file wherein the first housing half includes a centrally located transducer holder, and the bone-conduction transducer is seated in the centrally located transducer holder.

2. The sound therapy device of claim 1 wherein the stored audio file includes a compressed audio file of a pure tone.

3. The sound therapy device of claim 2 wherein the stored audio file includes an MP3 file or MP4 file.

4. The sound therapy device of claim 1 wherein the housing is disc-shaped.

5. The sound therapy device of claim 1 wherein the transducer holder includes an arcuate wall extending circumferentially around a center axis of the housing.

6. The sound therapy device of claim 1 wherein the power supply includes a plurality of batteries distributed circumferentially around the centrally located transducer holder.

7. A wearable sound therapy device comprising:
a housing including a cord connector for attaching a loop cord to support the sound therapy device about a user's neck, such that the sound therapy device is freely positionable in contact with the body of the user at a range of locations; and
audio electronics resident in the housing, the audio electronics including:
a transducer in contact with a portion of the housing;
an audio file storage medium storing an audio file of a pure tone;
a power supply; and
a transducer control unit structured to energize the transducer to vibrate based on the stored audio file in a manner that bone-conducts sound to the body of the user when the housing is in contact with the user;
wherein the sound therapy device produces only the pure tone at each location of the range of locations.

8. A method for sound therapy comprising:
energizing a sound therapy device utilizing an internal power supply;
contacting the sound therapy device directly with the body of a user;
reading a stored audio file of a pure tone from an audio file storage medium of the sound therapy device;
energizing a transducer in the sound therapy device to vibrate based on the audio file, such that the transducer produces only the pure tone; and
bone-conducting only the pure tone to the user at a range of locations on the body of the user based on the energizing of the transducer.

9. The method of claim 8 wherein the reading of the audio file of the pure tone includes reading an MP3 or MP4 file, and the bone-conducting the pure tone to the user at the range of locations includes bone-conducting the pure tone to a jaw or wrist.

10. The method of claim 8 wherein the sound therapy device includes a cord positioned about the neck of the user.

11. The method of claim 10 wherein the cord is sized such that the sound therapy device is positionable on the user's body at a range of locations where a bone is near enough to a surface of the skin for bone conduction.

12. The method of claim 11, wherein the sound therapy device is positioned under the user's clothing.

13. The method of claim 8, wherein the vibration of the transducer is audible only to the user.

* * * * *